United States Patent
Schnell et al.

(10) Patent No.: US 7,574,895 B2
(45) Date of Patent: Aug. 18, 2009

(54) SENSOR FOR DETECTING PARTICLES IN A GAS STREAM AND METHOD FOR ITS MANUFACTURE

(75) Inventors: Frank Schnell, Gerlingen (DE); Ralf Schmidt, Gerlingen (DE); Uwe Glanz, Asperg (DE); Sabine Rösch, Ditzingen (DE); Helmut Marx, Hochdorf (DE); Katharina Schaenzlin, Rottenburg-Obernau (DE); Henrik Schittenhelm, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 193 days.

(21) Appl. No.: 10/576,683

(22) PCT Filed: Sep. 7, 2004

(86) PCT No.: PCT/DE2004/001985

§ 371 (c)(1),
(2), (4) Date: Dec. 21, 2006

(87) PCT Pub. No.: WO2005/050174

PCT Pub. Date: Jun. 2, 2005

(65) Prior Publication Data

US 2007/0119233 A1    May 31, 2007

(30) Foreign Application Priority Data

Nov. 18, 2003   (DE)   ............................... 103 53 860

(51) Int. Cl.
*G01N 27/02*   (2006.01)
*G01R 3/00*    (2006.01)

(52) U.S. Cl. .................................................... 73/28.01

(58) Field of Classification Search ................ 73/28.01, 73/61.71
See application file for complete search history.

(56) References Cited

U.S. PATENT DOCUMENTS

| 3,226,615 | A | * | 12/1965 | Nagel | ........................ 361/280 |
| 4,307,061 | A | * | 12/1981 | Sarholz | ........................ 422/94 |
| 4,656,832 | A | * | 4/1987 | Yukihisa et al. | ............... 60/303 |
| 5,240,618 | A | * | 8/1993 | Caldwell et al. | ............ 210/748 |
| 6,110,354 | A |   | 8/2000 | Saban et al. | |
| 6,634,210 | B1 | * | 10/2003 | Bosch et al. | ............... 73/23.33 |
| 2001/0035044 | A1 | * | 11/2001 | Larsson et al. | ............. 73/28.01 |

FOREIGN PATENT DOCUMENTS

| DE | 29 28 496 | 1/1981 |
| DE | 101 33 384 | 1/2003 |
| DE | 101 33 385 | 1/2003 |
| JP | 62045161 | 2/1987 |
| JP | 6016017 | 1/1994 |
| JP | 7027731 | 1/1995 |
| JP | 2003098136 | 4/2003 |
| JP | 2003121403 | 4/2003 |
| WO | WO 03/095999 | 11/2003 |

\* cited by examiner

*Primary Examiner*—Daniel S Larkin
(74) *Attorney, Agent, or Firm*—Kenyon & Kenyon LLP

(57) ABSTRACT

A soot particle sensor for an exhaust system of an internal combustion engine includes a first electrode device and a second electrode device. The electrode devices are situated at a distance from one another and are able to be exposed to the gas stream, at least in some areas. It is provided that the electrode devices are separated from each other by an intermediate layer made of an electrically insulating material, and the electrode devices have free edges that are set apart from each other by the thickness of the intermediate layer and are able to be exposed to the gas stream.

18 Claims, 4 Drawing Sheets

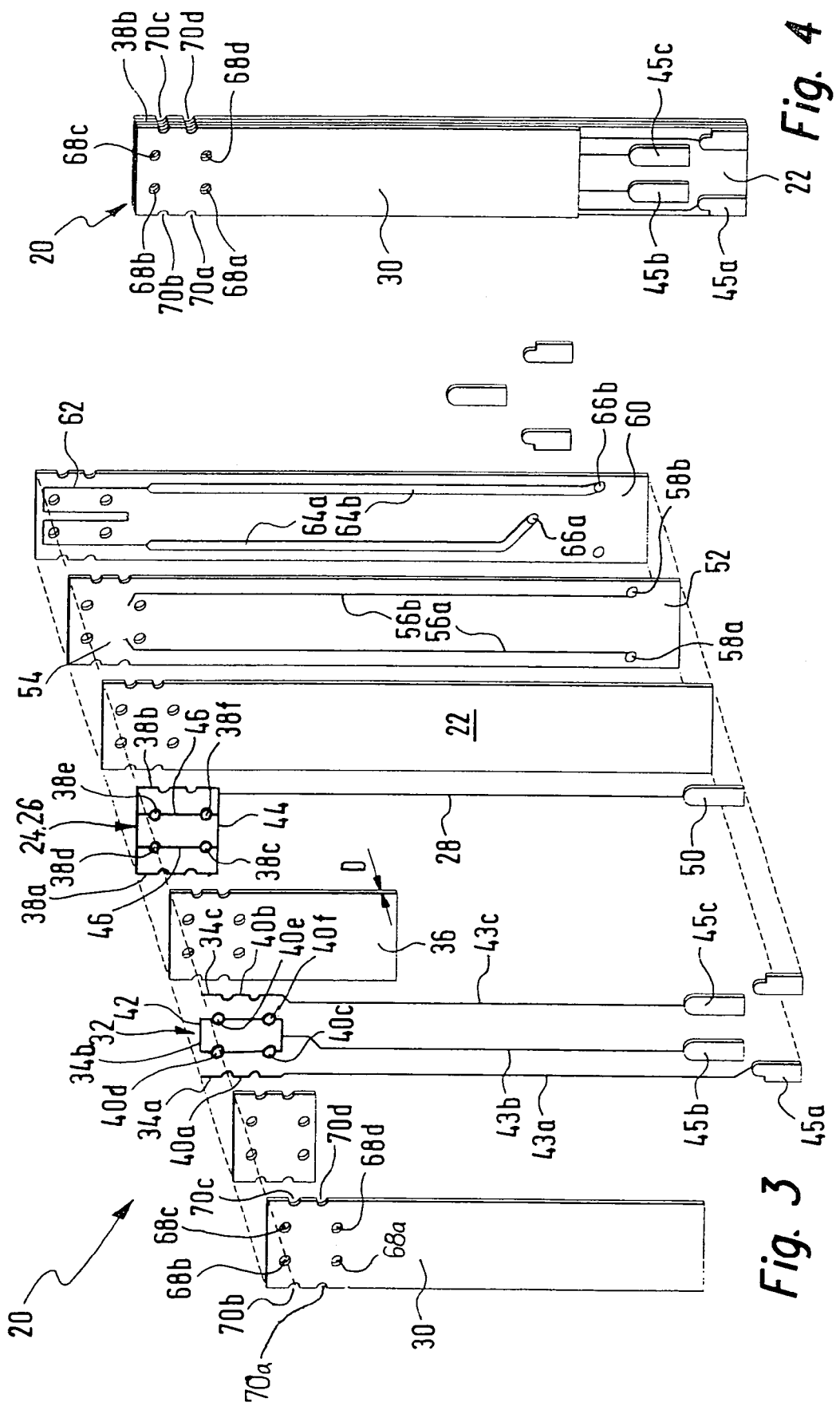

SENSOR FOR DETECTING PARTICLES IN A GAS STREAM AND METHOD FOR ITS MANUFACTURE

FIELD OF THE INVENTION

The present invention relates to a sensor for detecting particles in a gas stream, and relates particularly to a soot-particle sensor for an exhaust system of an internal combustion engine.

BACKGROUND INFORMATION

A sensor for detecting particles in an exhaust-gas stream is described in published German Patent Application DE 101 33 385. In the sensor described there, a collecting chamber is provided which can be coupled in fluid communication with an exhaust-gas stream of an internal combustion engine. A first electrode is situated on the upper side of the very flat collecting chamber, a second electrode on the lower side, thus opposite the first electrode. The collecting chamber between the two electrodes is hollow. When the known sensor is in operation, soot particles arrive in the collecting chamber and deposit in the hollow space between the two electrodes. The intervening space between the two electrodes is thereby electrically bridged, so that the impedance of the electrode structure changes. The change in impedance over time is a measure for the loading of the exhaust-gas stream with soot particles.

A sensor for detecting particles in an exhaust-gas stream is also described in published German Patent Application DE 101 33 384. There, the two electrodes are situated on the lower side of the collecting chamber and intermesh in comb-like fashion. The change in impedance between the two electrodes is a measure for the loading of the exhaust-gas stream with soot here, as well.

The sensor must be highly sensitive to precisely detect the loading of an exhaust-gas stream with soot. In this context, it holds true that the smaller the distance between the two electrodes, the more sensitive the sensor. In the case of the two known sensors described above, the distances between the two electrodes ("GAP") are typically 30 to 100 μm. A further reduction in distances between the two electrodes is difficult from the standpoint of production engineering in the case of the known sensors, and can lead to durability problems during operation.

Therefore, an object of the present invention is to develop a sensor in such a way that it can be produced inexpensively, has a long service life, and at the same time, is able to detect the loading of a gas stream with particles with great accuracy.

SUMMARY

In a sensor according to the present invention, the electrode devices are separated from each other by an intermediate layer made of an electrically insulating material, and the electrode devices have free edges that are set apart from each other by the thickness of the intermediate layer and are able to be exposed to the gas stream.

In the sensor of the present invention, a small distance can also be precisely realized between the two electrode devices, since this distance is predefined by the intermediate layer made of the electrically insulating material. Because it is possible to set the electrode devices in the sensor of the present invention apart from each other only up to a few micrometers, which in principle corresponds to a capacitor-like construction, the sensor exhibits great sensitivity and low response time, which permits particularly precise detection of particles in a gas stream. At the same time, the carrier structures of the electrode devices can be designed to be sturdy such that the sensor has a long service life. Moreover, it is comparatively inexpensive to manufacture the sensor of the present invention, since the distance between the electrodes is "automatically" predefined by the intermediate layer, and does not have to be achieved by complex production methods.

The realization of the indicated advantages is achieved by the intermediate layer already mentioned, with whose aid it is also possible to reliably implement the smallest distances between the two electrode devices, and, by the fact that the actual sensor surfaces are formed by the lateral, exposed edges of the electrode devices. By decreasing the abrasive erosion on the surfaces of the electrodes, and reducing the effects of such erosion, the service life is increased.

It is particularly advantageous if the intermediate layer includes a foil or a thick film. Foils made of electrically insulating material having extremely small wall thicknesses, as well, are commercially available. Moreover, it is comparatively easy to manipulate such a foil. Overall, therefore, production is simplified and inexpensive. Particularly small wall thicknesses may be realized using thick-film technology.

It may also be provided that at least one of the two electrode devices includes a plurality of individual electrodes. This provides several advantages: First of all, the operational reliability of the sensor can thus be increased, since the individual electrodes result in a redundant overall system.

Secondly, it is possible to check the functioning of one individual electrode by comparing the signal of at least one of the individual electrodes, especially if their free edges are situated at different locations, the particle loading of the gas stream may be detected particularly precisely.

A further advantageous example embodiment of the sensor according to the present invention provides that free electrode-device edges able to be exposed to the gas stream are disposed at: at least one free outer edge of the sensor; and/or at least one through-hole; and/or at least one blind-hole-like opening in the sensor.

This permits optimal adaptation of the sensor to the individual flow and installation conditions of the device in which the gas stream is to be measured. Moreover, the specified free edges may be easily produced by boring, cutting, punching, etc.

Production is again simplified if the electrode devices are each imprinted on a foil. This foil may at the same time be used as the electrically insulating intermediate layer.

In an example embodiment, the sensor may include a heating device, and by heating the free edges of the electrode device, particles deposited there may easily be burned off, so that it is then possible to begin again with a new measuring cycle without having to exchange the sensor.

In an example embodiment of the present invention, it is advantageous if the sensor also includes a temperature-sensing device. It may be used to monitor the heating process, so that damage to the sensor due to heating may be avoided.

In this context, it is especially advantageous if the heating device and/or the temperature-sensing device is/are in each case imprinted on a foil. This simplifies production and lowers production costs.

An example method for manufacturing a sensor according to the present invention may include the following steps:
 a) the first electrode device is applied on a first carrier;
 b) the second electrode device is applied on a second carrier;
 c) an intermediate layer made of an electrically insulating material is applied on the side of the first carrier on which the first electrode device is applied;

d) the second carrier having the second electrode device is arranged on the intermediate layer made of the electrically insulating material in such a way that the side of the second carrier on which the second electrode device is applied points toward the intermediate layer made of the electrically insulating material;

e) the carriers and layers placed one upon the other are joined to each other (laminated);

f) the laminate of the carriers and layers is processed in such a way that it has exposed, adjacent edges of the internal electrode devices, the edges being set apart from each other only by the thickness of the intermediate layer made of the electrically insulating material.

Such a foil technology method makes it possible to manufacture a sensor inexpensively, precisely and rapidly.

Alternatively, an example method according to the present invention may include the following steps:

a) the first electrode device is applied on a first carrier;

b) at least one insulating intermediate layer is applied on the first electrode device;

c) the second electrode device is applied on the insulating intermediate layer;

d) a protective layer is applied on the second electrode device;

e) the carrier and layers placed one upon the other are joined to each other (laminated);

f) the laminate of the carrier and layers is processed in such a way that it has exposed, adjacent edges of the electrode devices, the edges being set apart from each other only by the thickness of the intermediate layer made of the electrically insulating material.

This example method is particularly fast and inexpensive.

In a further development, in step f), it is provided that the laminate is cut or punched or bored. This makes it possible to produce the free edges of the electrode devices in a simple manner.

It is likewise possible that, prior to placing the carriers one upon the other, a combustible material is applied at least on the first carrier and on the intermediate layer made of electrically insulating material at at least one location at which the electrode devices are intended to have free edges, and the laminate is later heated so that the combustible material burns and, in so doing, the area of the carrier and of the intermediate layer, respectively, on which it was applied, also burns. In this case, the free edges of the electrode devices that are exposed to the gas stream during operation are produced by a sintering method. In this way, blind-hole-type openings may be introduced very easily, as well.

BRIEF DESCRIPTION OF THE DRAWINGS

FIG. 3 is an exploded perspective view of a further example embodiment of the soot-particle sensor included in FIG. 1.

FIG. 4 shows a perspective view of the soot-particle sensor of FIG. 3 in the assembled state.

DETAILED DESCRIPTION

Figure 1:
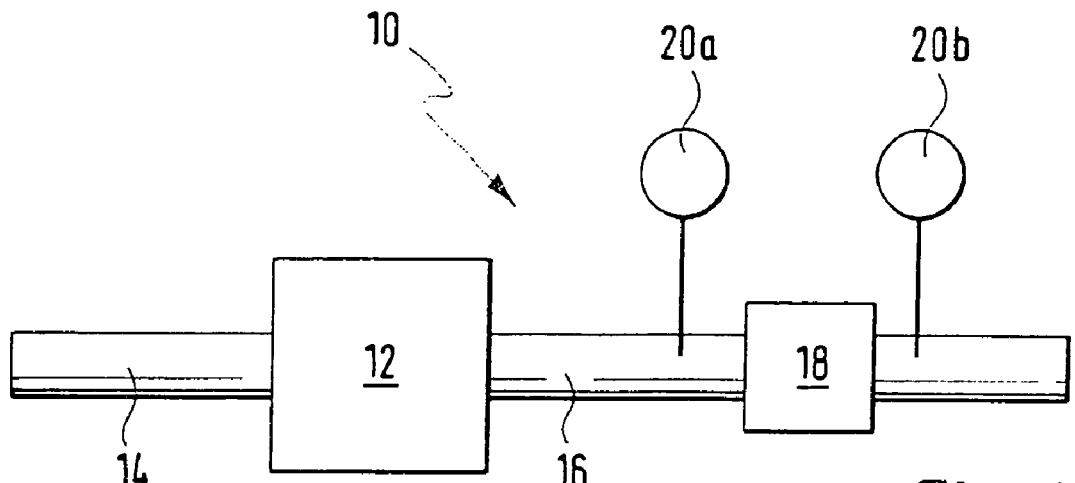
FIG. 1 shows a schematic representation of an internal combustion engine having an exhaust pipe and a soot-particle sensor.

In FIG. 1, an internal combustion engine is designated generally by reference numeral 10. It includes an engine block 12, an intake manifold 14 and an exhaust pipe 16. Internal combustion engine 10 may be a diesel engine, for example. A soot-particle filter 18 is situated in its exhaust pipe 16.

Soot particles in the exhaust gas are stopped and collected by soot-particle filter 18. For reliable operation of internal combustion engine 10, it is necessary to detect a state in which soot-particle filter 18 has picked up so many soot particles that its permeability is restricted and, because of the filter loading, regeneration can no longer be ensured. If such a situation is recognized, soot-particle filter 18 must either be replaced or regenerated. To permit detection of such a situation, soot-particle sensors 20a and 20b are situated upstream and downstream of soot-particle filter 18 in exhaust pipe 16. They detect the loading of the exhaust gas with soot particles at the corresponding locations in exhaust pipe 16, and thus make it possible to estimate the loading of soot-particle filter 18 with soot particles and to monitor the correct functioning of soot-particle filter 18.

Figure 2:
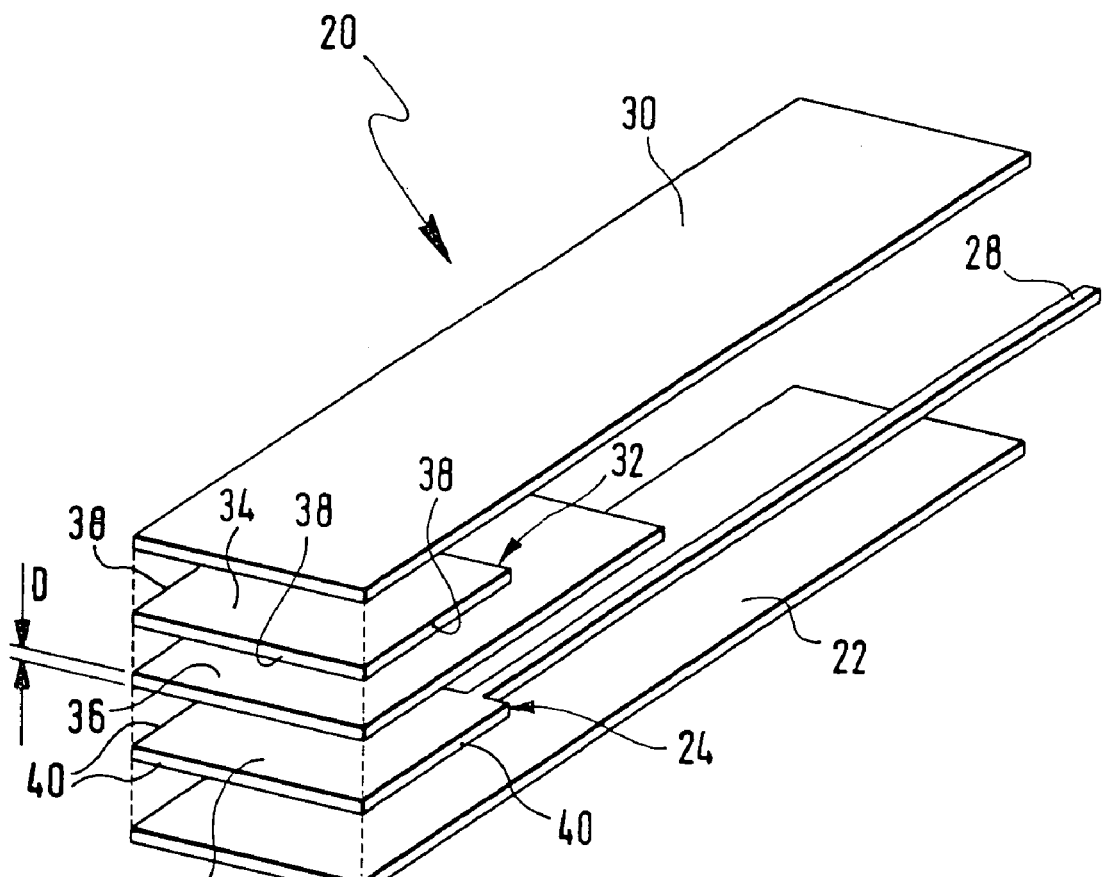
FIG. 2 is an exploded perspective view of an example embodiment of the soot-particle sensor included in FIG. 1.

Soot-particle sensors 20a and 20b may be constructed according to the exemplary embodiment (generally designated 20) shown in FIG. 2: Soot-particle sensor 20, shown in FIG. 2 in an exploded perspective view, has a first ceramic carrier 22. The carrier has an elongated, rectangular horizontal projection and is a few tenths millimeter thick. Carrier 22 is thus basically a ceramic foil. A first electrode device 24 is imprinted on ceramic carrier 22. It includes an electrode 26, approximately square in the plan view, which is applied to the left, i.e., front end of ceramic carrier 22 in FIG. 2, and laterally, is exactly as wide as ceramic carrier 22 and is flush with its front edge in the figure. First electrode device 24 also has a lead 28 which extends to first electrode 26.

Soot-particle sensor 20 has a second ceramic carrier 30 which is substantially identical to first ceramic carrier 22. Imprinted on it is a second electrode device 32 whose only difference with respect to first electrode device 24 is that the lead to second electrode 34 is situated in the area of the rear edge in FIG. 2, and is therefore covered by second ceramic carrier 30 in the view shown in FIG. 2.

Situated between the two electrodes 26 and 34 is an intermediate layer 36 made of an electrically insulating material. It is exactly the same width as the two electrodes 26 and 34, and likewise extends up to the front end of sensor 20 in FIG. 2. However, the layer 36 is somewhat longer than the two electrodes 26 and 34, and therefore extends beyond the inner edge of the two electrodes 26 and 34 in the direction of lead 28 and the non-visible lead to second electrode 34. This ensures that no electrical contact exists between the two electrode devices 24 and 32 within sensor 20. Intermediate layer 36 is comparatively thin, its thickness D being several micrometers, for example. For example, thick-film technology may be used to implement it. Optionally, a foil may also be used.

Sensor 20 shown in FIG. 2 may be produced by first applying first electrode device 24 on first ceramic carrier 22, and second electrode device 32 on second ceramic carrier 30. Intermediate layer 36 is then applied on the composite construction made of first electrode device 24 and first ceramic carrier 22, and the composite construction made of second ceramic carrier 30 and second electrode device 32 is put on. The individual elements of this stack are permanently bonded to each other by a thermal adhesive process or sintering process, for instance.

Alternatively, sensor 20 may also be produced using thick-film technology. In this case, carrier 30 may also simply be a protective and insulating layer.

The lateral edges of ceramic carriers 22 and 30, electrode devices 24 and 32, and intermediate layer 36 may initially still be relatively imprecise. The final lateral edges corresponding to the view in FIG. 2 are produced, for example, by sawing or punching after the laminate or layer stack has been produced. Finished soot-particle sensor 20 then has two electrodes 26 and 34 which, in the plan view, are situated directly over one another and at a distance D from one another, distance D being predefined by the thickness of intermediate layer 36. Electrodes 26 and 34 of finished soot-particle sensor 20 each have three exposed, straight edge surfaces 38 and 40, respectively, whose height corresponds to the thickness of electrodes 26 and 34. Edge surfaces 40 of first electrode 26 are exactly set apart from edge surfaces 38 of second electrode 34 by distance D.

When exhaust gas loaded with soot particles flows past the two soot-particle sensors 20a and 20b of FIG. 1 assembled according to FIG. 2, soot particles also deposit on both sensors 20a and 20b. This results in a progressive electrical bridging of distance D between edge surfaces 40 of first electrode 26 and edge surfaces 38 of second electrode 34. Therefore, the impedance of the device formed of the two electrodes 26 and 34 changes, which is detectable by a detector connected to the two electrodes 26 and 34 via lead 28 and the lead not visible in FIG. 2. Since the distance between adjacent edge surfaces 38 and 40 is extremely small, soot-particle sensors 20a and 20b exhibit great sensitivity.

An alternative example embodiment of a soot-particle sensor 20 will now be explained with reference to FIGS. 3 and 4. In this context, it holds true here and in the following that those elements and regions which have functions equivalent to functions and regions of previous figures, i.e., FIGS. 1 and 2, bear the same reference numerals and are not explained again in detail.

A first difference of sensor 20 shown in FIG. 3 compared to that of FIG. 2 relates to the form of second electrode device 32. Namely, it includes a total of three individual electrodes 34a, 34b and 34c which are separate from each other and have a linear design. The two electrodes 34a and 34c are situated on the two opposite lateral edges of sensor 20. Electrode 34b includes a ring circuit 42 and four initially whole-surface conductor points that are situated relative to each other in such a way that they form the corners of an imaginary rectangle. The whole-surface conductor points are disposed in ring circuit 42 and bear no reference numerals in FIG. 3. They will be discussed in greater detail below. Each electrode 34a, 34b and 34c has a separate lead 43a, 43b and 43c having corresponding electrical connection contacts 45a, 45b and 45c.

First electrode 26 of electrode device 24 likewise includes a ring circuit 44 which, in plan view, is square. An upper and a lower section of ring circuit 44 in FIG. 3 are interconnected via two connecting lines 46 that are vertical in FIG. 3, and thus extend in the longitudinal direction of sensor 20. Likewise provided in them are in each case two whole-surface conductor points which, in the plan view, lie exactly below those of electrode device 32, and which are discussed in greater detail below. A connecting line to first electrode 26 bears reference numeral 28 in FIG. 3, and a corresponding connection contact bears reference numeral 50.

Element 30 may be a carrier, or else simply an insulating and/or protective layer. A further difference of sensor 20 shown in FIG. 3 with respect to that of FIG. 2 is that the sensor shown in FIG. 3 additionally has a foil 52, on which a temperature sensor 54 is imprinted. Connection leads 56a and 56b of temperature sensor 54 lead into circular contact points 58a and 58b. Foil 52 is applied on first carrier foil 22, on its side facing away from first electrode 26.

Sensor 20 further has an additional foil 60, on which a heating conductor 62 is imprinted. Connection leads 64a and 64b of heating conductor 62 lead ti connection contacts 66a and 66b. When sensor 20 is assembled, temperature sensor 54 and heating conductor 62 are situated in the immediate vicinity of the two electrodes 26 and 34.

The sensor shown in FIG. 3 is manufactured similarly to that of the sensor shown in FIG. 2. However, after the individual layers have been joined, the finished laminate is worked using a drilling tool to drill through-holes into the laminate perpendicular to the planes of carriers 22 and 30 exactly at those locations at which the whole-surface conductor points of electrodes 26 and 34 are located. The through-holes bear reference numerals 68a through 68d in FIGS. 3 and 4. The lateral edges of the laminate, after being precisely produced by punching, sawing or cutting, for instance, are also worked by the drilling tool in the region of outer, second electrodes 34a and 34c. Recesses 70a through 70d having a semicircular cross-section and extending perpendicular to the plane of carriers 22 and 30 thereby result. Typically, sensor 20 is approximately 60 mm long, 1 to 2 mm high, and 4 to 8 mm wide. The free edges of second electrode device 32 that are able to be exposed to the gas stream in exhaust pipe 16 now result at the following locations: First, at the lateral, longitudinally-extending edge of sensor 20 in the region of linear electrodes 34a and 34c (where they bear reference numerals 40a and 40b), and secondly in the region of through-holes 68a to 68d at those places where the whole-surface, circular conductor points were present in ring circuit 42. These ring-shaped, exposed edge surfaces bear reference numerals 40c to 40f. Analogous thereto, the exposed edge surfaces of first electrode 26 are formed at the lateral, longitudinally-extending edges (reference numerals 38a and 38b), and, on the basis of through-holes 68a to 68d, in the region of the originally whole-surface, circular conductor points in connecting lines 46. They bear reference numerals 38c to 38f.

It is easy to see that sensor 20 shown in FIGS. 3 and 4 has a plurality of exposed edge-surface pairs 38 and 40 of electrodes 26 and 34—the edge-surface pairs being able to be exposed to the gas stream in exhaust pipe 16 and being set apart from each other only by the thickness D of intermediate layer 36—whose impedance changes with increasing particle loading, and which thus supply a signal for the particle loading of the exhaust gas flowing in exhaust pipe 16. In this context, recesses 70a to 70d, as well as through-holes 68a to 68d, offer particularly favorable flow conditions. An abrasive removal of electrode material, which shortens the service life, is reduced, and furthermore, has almost no influence on the sensor signal. Heating conductor 62 situated in the region of through-holes 68a to 68d is able to ensure optimal burn-off, especially of ring-shaped, free edge surfaces 68c to 68f and 40c to 40f.

Figure 5:
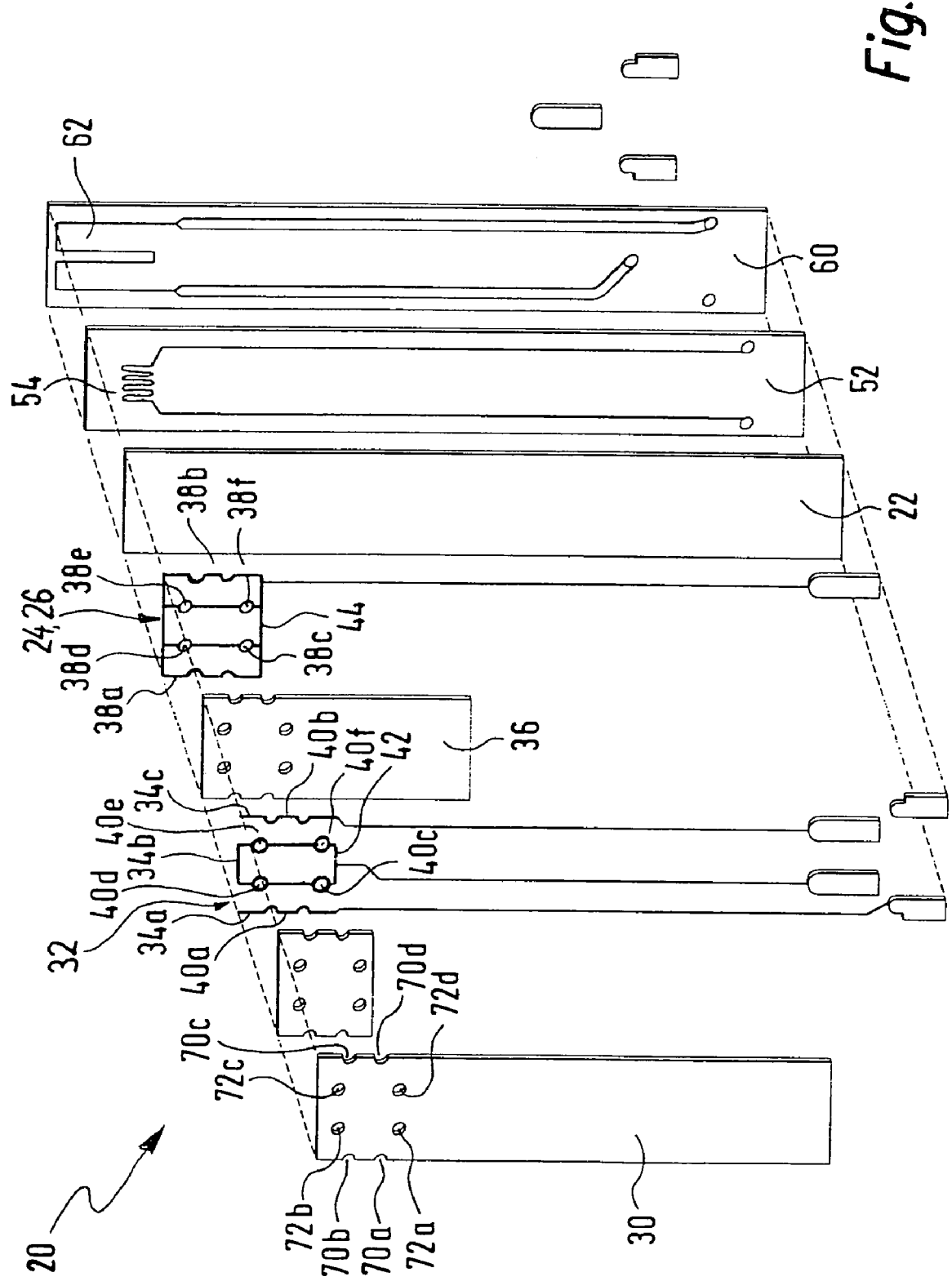
FIG. 5 is an exploded perspective view of a further example embodiment of a soot-particle sensor.

An alternative example embodiment is shown in FIG. 5. It differs from sensor 20 shown in FIGS. 3 and 4, in that the holes take the form of blind holes, and therefore bear reference numerals 72a to 72d. First carrier 22 and foil 52 and foil 60 do not have these holes. This can have advantages from the standpoint of fluid mechanics in certain installation situations. Blind holes 72a to 72d are produced by printing a soot-filled paste onto ceramic carrier 30 and intermediate layer 36 prior to joining the individual layers of sensor 20. During the process of thermally bonding the individual layers by sintering, these material points burn and leave behind the holes, shown in FIG. 5, in the respective structures. However, this assumes that the individual elements of the layer structure, from which sensor 20 is constructed, are laterally aligned with the utmost precision, so that the holes in the individual layers ultimately yield continuous blind holes 72a to 72d having inner, free edges 38 and 40.

Figure 6:
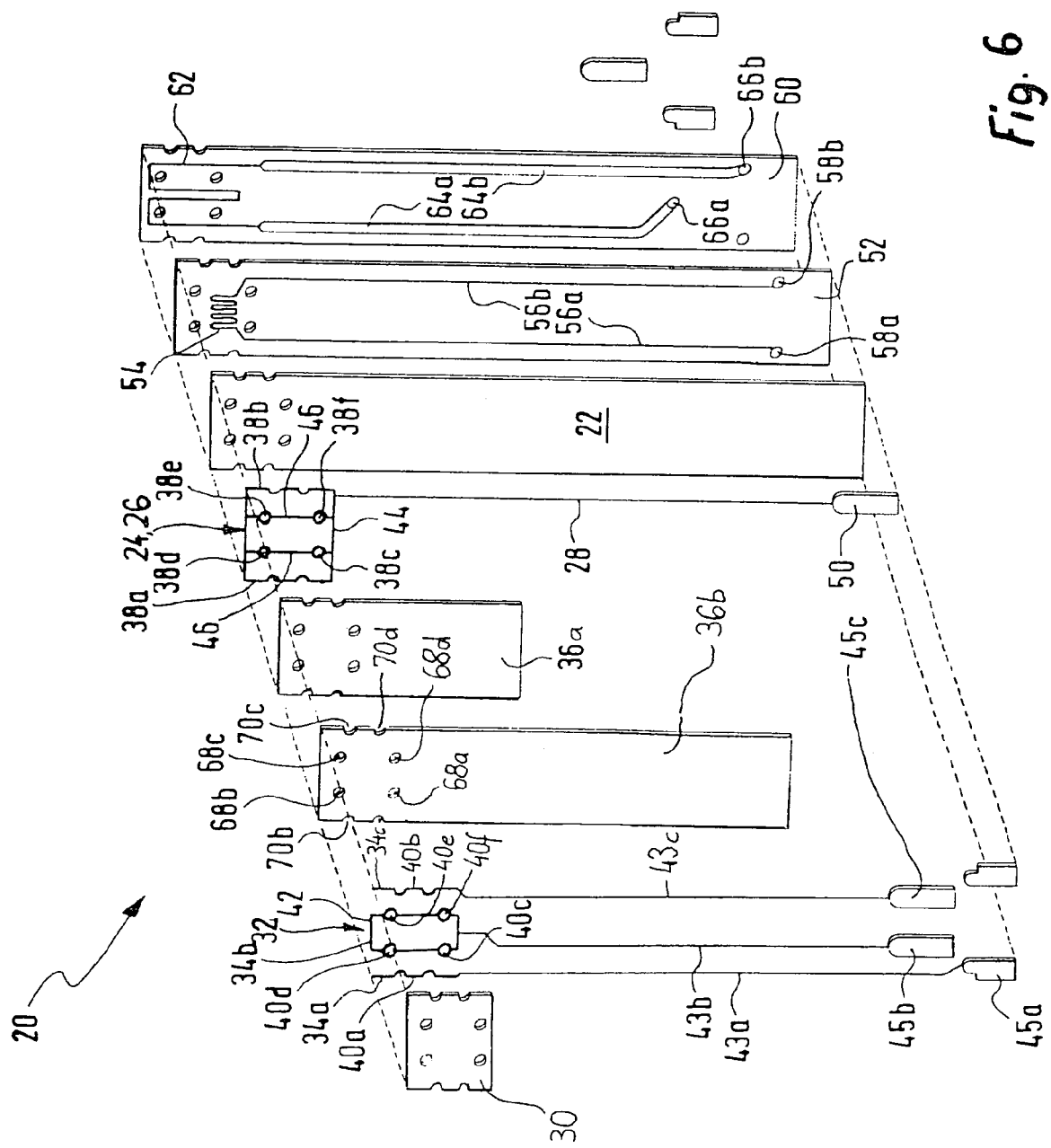
FIG. 6 is an exploded perspective view of a further example embodiment of a soot-particle sensor.

FIG. 6 shows a soot-particle sensor 20 manufactured in the following example manner: First, first electrode device 24 is imprinted on first carrier 22. Thereupon, using thick-film technology, for example, first electrode device 24 has applied to it two insulating intermediate layers 36a and 36b, upon which, in turn, second electrode device 32 is positioned. Finally, second electrode device 32 is covered with a protective layer 30.

Carrier 22 and layers 30, 36a and 36b situated one upon the other are now joined together by laminating. The laminate resulting therefrom is processed in such a way that it has exposed, adjacent edges 38, 40 of electrode devices 24, 32, the edges being set apart from each other only by the thickness of intermediate layers 36a and 36b made of the electrically insulating material.

What is claimed is:

1. A sensor for detecting particles in a gas stream, comprising:
   a first electrode device;
   a second electrode device situated at a specified vertical distance from the first electrode device, wherein at least portions of the first and second electrode devices are configured to be exposed to the gas stream; and
   an intermediate layer separating the first and second electrode devices;
   wherein;
      the specified distance between the first and second electrode devices corresponds to the thickness of the intermediate layer;
      the intermediate layer includes an electrically insulating material; and
      portions of edges of the first and second electrode devices are configured to be exposed to the gas stream.

2. The sensor as recited in claim 1, wherein the intermediate layer includes one of a foil and a thick film.

3. The sensor as recited in claim 2, wherein at least one of the first and second electrode devices includes a plurality of individual electrodes.

4. The sensor as recited in claim 3, wherein the portions of the edges of the first and second electrode devices configured to be exposed to the gas stream are situated at least one of: a) at a free outer edge of the sensor; b) at a through-hole in the sensor; and c) at a blind-hole-type opening in the sensor.

5. The sensor as recited in claim 2, wherein the portions of the edges of the first and second electrode devices configured to be exposed to the gas stream are situated at least one of: a) at a free outer edge of the sensor; b) at a through-hole in the sensor; and c) at a blind-hole-type opening in the sensor.

6. The sensor as recited in claim 5, wherein each of the first and second electrode devices is imprinted onto a foil.

7. The sensor as recited in claim 6, further comprising:
   a heating device.

8. The sensor as recited in claim 7, further comprising:
   a temperature-sensing device.

9. The sensor as recited in claim 8, wherein at least one of the heating device and the temperature-sensing device is imprinted onto a foil.

10. A method for manufacturing a sensor for detecting particles in a gas stream, comprising:
    a) applying a first electrode device on a first carrier;
    b) applying a second electrode device on a second carrier;
    c) applying an intermediate layer including an electrically insulating material on the side of the first carrier on which the first electrode device is applied;
    d) arranging the second carrier having the second electrode device on the intermediate layer in such a way that the side of the second carrier on which the second electrode device is applied faces the intermediate layer;
    e) laminating the first electrode device having the first carrier, the second electrode device having the second carrier, and the intermediate layer to each other to create a laminate product; and
    f) processing the laminate product in such a way that adjacent edges of the first and second electrode devices are exposed and set apart from each other only by the thickness of the intermediate layer.

11. The method as recited in claim 10, wherein in step f), the laminate product is one of cut, punched and bored.

12. The method as recited in claim 10, further comprising:
    prior to step d), applying a combustible material at least on the first carrier and on the intermediate layer at each location at which the first and second electrode devices are intended to have exposed edges; and
    heating the laminate product such that burning of the combustible material and corresponding location of the first carrier and the intermediate layer on which the combustible material was applied occurs.

13. A method for manufacturing a sensor for detecting particles in a gas stream, comprising:
    a) applying a first electrode device on a first carrier;
    b) applying at least one insulating intermediate layer on the first electrode device;
    c) applying a second electrode device on the insulating intermediate layer;
    d) applying a protective layer on the second electrode device;
    e) laminating the first electrode device having the first carrier, the second electrode device, the insulating intermediate layer, and the protective layer to each other to create a laminate product; and
    f) processing the laminate product in such a way that adjacent edges of the first and second electrode devices are exposed and set apart from each other only by the thickness of the insulating intermediate layer.

14. The method as recited in claim 13, wherein in step f), the laminate product is one of cut, punched and bored.

15. The method as recited in claim 13, further comprising:
    prior to step d), applying a combustible material at least on the first carrier and on the insulating intermediate layer at each location at which the first and second electrode devices are intended to have exposed edges; and
    heating the laminate product such that burning of the combustible material and corresponding location of the first carrier and the insulating intermediate layer on which the combustible material was applied occurs.

16. A sensor for detecting particles in a gas stream, comprising:
    a first electrode device applied on a side of a first carrier;
    a second electrode device applied on a side of a second carrier;
    an intermediate layer applied on the side of the first carrier on which the first electrode device is applied;
    wherein:
       the intermediate layer includes an electrically insulating material;

the second carrier is arranged on the intermediate layer in such a way that the side of the second carrier on which the second electrode device is applied faces the intermediate layer;

the first electrode device having the first carrier, the second electrode device having the second carrier, and the intermediate layer are laminated to each other forming a laminate product; and the laminate product is processed such that adjacent edges of the first and second electrode devices are exposed and set apart from each other only by the thickness of the intermediate layer.

17. A sensor for detecting particles in a gas stream, comprising:

a first electrode device applied on a side of a first carrier, and wherein at least one insulating intermediate layer is applied on the first electrode device;

a second electrode device applied on a side of the insulating intermediate layer;

a protective layer is applied on the second electrode;

the insulating intermediate layer separating the first and second electrode devices;

wherein:

the insulating intermediate layer includes an electrically insulating material;

the first electrode device having the first carrier, the second electrode device having the second carrier, and the intermediate layer are laminated to each other forming a laminate product; and the laminate product is processed such that adjacent edges of the first and second electrode devices are exposed and set apart from each other only by the thickness of the insulating intermediate layer.

18. A sensor for detecting particles in a gas stream, comprising:

a first electrode device;

a second electrode device situated at a specified vertical distance from the first electrode device, wherein at least portions of the first and second electrode devices are configured to be exposed to the gas stream;

a detector detecting an impedance between the first and second electrode devices; and an intermediate layer separating the first and second electrode devices;

wherein:

the specified distance between the first and second electrode devices corresponds to the thickness of the intermediate layer;

the intermediate layer includes an electrically insulating material; and portions of edges of the first and second electrode devices are configured to be exposed to the gas stream.

* * * * *

UNITED STATES PATENT AND TRADEMARK OFFICE
CERTIFICATE OF CORRECTION

PATENT NO. : 7,574,895 B2  Page 1 of 1
APPLICATION NO. : 10/576683
DATED : August 18, 2009
INVENTOR(S) : Schnell et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 276 days.

Signed and Sealed this

Seventh Day of September, 2010

David J. Kappos
*Director of the United States Patent and Trademark Office*